United States Patent [19]
White

[11] 4,369,117
[45] Jan. 18, 1983

[54] SERUM SEPARATING METHOD AND APPARATUS

[75] Inventor: Fred K. White, Miami, Fla.

[73] Assignee: American Hospital Supply Corporation, Evanston, Ill.

[21] Appl. No.: 148,815

[22] Filed: May 12, 1980

[51] Int. Cl.³ .............................................. B01D 21/26
[52] U.S. Cl. .................................. 210/782; 210/927; 210/360.1; 210/508; 210/DIG. 24
[58] Field of Search ....... 210/782, 927, 516, DIG. 24, 210/508

[56] References Cited

U.S. PATENT DOCUMENTS

| | | | |
|---|---|---|---|
| 2,794,239 | 6/1957 | Crawford et al. | 210/508 X |
| 3,647,070 | 3/1972 | Adler | 210/516 |
| 3,733,179 | 5/1973 | Guehlea | 210/927 X |
| 3,852,194 | 12/1974 | Zine | 210/DIG. 24 |
| 3,901,402 | 8/1975 | Ayres | 210/927 |
| 3,909,419 | 9/1975 | Ayers | 210/518 |
| 3,919,085 | 11/1975 | Ayres | 210/516 |
| 3,920,557 | 11/1975 | Ayres | 210/516 |
| 3,929,646 | 12/1975 | Adler | 210/359 |
| 3,931,018 | 1/1976 | North, Jr. | 210/359 |
| 3,951,798 | 4/1976 | Haldopoulos | 210/927 |
| 3,951,801 | 4/1976 | Ayres | 210/117 |
| 3,957,654 | 5/1976 | Ayres | 210/516 |
| 3,986,962 | 10/1976 | Kessler | 210/516 |
| 4,001,122 | 1/1977 | Griffin | 210/516 |
| 4,012,325 | 3/1977 | Columbus | 210/516 |
| 4,055,501 | 10/1977 | Cornell | 210/516 |
| 4,088,582 | 5/1978 | Murty | 210/516 |
| 4,246,107 | 1/1981 | Takenaka et al. | 210/927 X |

Primary Examiner—John Adee
Attorney, Agent, or Firm—Tilton, Fallon, Lungmus

[57] ABSTRACT

A method and apparatus for separating serum from other blood components in a centrifuge tube. The separator comprises a cylindrical, laterally-expandable filter element composed of a multiplicity of generally longitudinally-oriented fibers, 10 to 40 millimicrons in diameter, formed of a biologically inert polymeric material having a specific gravity within the range of about 1.10 to 1.50 and bonded to adjacent fibers only at spaced-apart junctures. The filter element has a diameter within the range of 9 to 15 millimeters, a length from 75 to 125 percent of its diameter, and a bulk density of about 0.20 to 0.60 grams per cubic centimeter. During centrifugation, the filter advances downwardly from the mouth of the centrifuge tube, swelling laterally as serum flows through the fine passageways running generally lengthwise of the filter, and causing the descending filter to wipe against the walls of the tube, pushing loose cells and fibrin ahead of it, and finally compacting and restraining the fibrin-cell clot at the bottom of the tube to permit subsequent decantation of the filtered serum. In one embodiment, the filter is introduced into the tube by means of a stretchable cap which serves as a carrier for the filter prior to insertion and as a protective cover for the tube thereafter.

25 Claims, 10 Drawing Figures

SERUM SEPARATING METHOD AND APPARATUS

BACKGROUND

For a number of years, especially since the advent of automated clinical analyses, there has been a need for simple and inexpensive means to separate serum from the other constituents of coagulated blood so that various diagnostic tests may be performed on the serum without danger that particulates in the fluid may cause malfunctioning and possible breakdown of the complex and costly automated analysis equipment, or produce incorrect and misleading test results, or both. Although the problems have been recognized in the past, the proposed solutions to those problems have all had major shortcomings.

In one type of centrifugally-activated system, a specially-prepared centrifuge tube (which may also be stoppered, air-evacuated, and serve as a blood collection tube) contains a mass of viscous thixotropic gel at its lower (closed) end. The gel has a specific gravity between that of serum (1.03) and the heavier cellular components (1.09). Therefore, when a blood-filled tube is centrifuged the contents will stratify with the gel assuming a position between the serum (or plasma) and the cellular components. See, for example U.S. Pat. No. 3,852,194. While such a system does result in the formation of a barrier between serum (or plasma) and the solid constituents, no filtering action, and no wiping or cleaning of the tube surfaces above the equilibrium position of the gel barrier, take place. Residual fibrin and cells may remain in the serum layer, either clinging to the wall of the tube or floating freely and, in either event, providing a source of interference during subsequent testing of the serum (or plasma) layer.

In an effort to reduce such problems, serum separators have been devised in which the thixotropic gel is introduced from the stoppered upper end of the tube, rather than from the closed lower end, and migrates downwardly during centrifugation to assume its equilibrium position at the serum-clot interface. (See U.S. Pat. Nos. 3,986,962, 4,055,501, 3,957,654, 3,647,070, 4,012,325). Again, however, in such a system the gel performs no significant wiping and filtering actions. In general, such gel systems not only fail to provide a clean separation between the liquid and solid components of blood, but they also have the further disadvantages of being relatively expensive and having only a limited (approximately six months) shelf life.

In another type of centrifugally-activated serum separating device, a piston is fitted into a centrifuge tube, the piston having a specific gravity between that of serum (1.03) and red cells (1.09). The piston has a resilient tube-contacting periphery and is also provided with one or more openings so that during centrifugation it will migrate from the upper end of the tube into an intermediate equilibrium position at the serum-clot interface. See U.S. Pat. Nos. 3,931,018, 3,951,801, 4,001,122. Such piston-type separators are capable of performing effective separating and wiping actions but only if the tubes are dimensioned to close tolerances, thereby necessitating the use of special tubes which, added to the cost of the separator, result in a relatively expensive assembly.

Other types of centrifugally-activated separators, some of which combine gel barriers with piston-like structures, and others which function as separators only when they are subjected to a further treatment (such as heat treatment) after they have assumed their equilibrium positions, are represented by U.S. Pat. Nos. 4,088,582, 3,909,419, 3,926,646, 3,920,557, and 3,919,085. Generally, most of such centrifugally-activated separators, whether utilizing a gel, or an apertured piston, or a combination of both, are automatically interface-seeking because their specific gravity is set or adjusted at about 1.06, at a point between the specific gravities of serum (or plasma) and the heavier non-fluid blood components.

SUMMARY OF INVENTION

One important aspect of this invention lies in the discovery that a superior interface-seeking separator may be obtained by utilizing a fibrous laterally-expandable cylindrical filter element or plug composed of an inert polymeric material having a specific gravity significantly greater than all of the blood components, including the heavier cellular components. Such a filter element, when properly constructed and used in accordance with this invention, provides effective wiping and filtering actions and produces a clean separation between the serum layer and the particulate layer. Furthermore, such a separator is relatively inexpensive and is self-adjusting in use so that special tubes manufactured to closer tolerances than standard tubes are not required.

A significant additional feature of this invention lies in providing a method and apparatus which are operative to separate the cellular and liquid components of blood only if such blood is capable of coagulating under normal conditions. Thus, should a sample to be tested have been drawn from a patient whose blood resists coagulation because of hemophilia, anticoagulation therapy, or any other reason, the serum separator of this invention, unlike other separating devices and methods, will allow red cells to remain in the upper stratum as a clear visual indication of the patient's condition.

In a basic mode of practicing the invention, a sample of fresh blood is first collected or placed in a tube capable of being received by the tube carrier of a conventional hematological centrifuge. Such tube may be the standard 100×13 or 100×16 (in millimeters) laboratory tubes commonly used for blood collection. After an interval of approximately 30 minutes or more to allow for coagulation, a laterally-expandable cylindrical filter element is introduced into the mouth of the tube, and the tube and its contents are then centrifuged to cuase the element to migrate to the bottom of the tube behind the matrix or clot of frbrin and cells. As the filter descends, serum flows upwardly between the generally longitudinally oriented fibers causing the loosely bonded fibers to separate slightly and increasing the transverse dimensions of the filter as a whole. Consequently, the cylindrical filter, which fit loosely into the mouth of the tube at the outset, expands laterally and wipes the walls of the tube free of loose cells and residual fibrin strands.

As the filter enters the lower portion of the tube it begins to compress the clot because of the higher specific gravity of the polymeric material from which the fibrous filter is formed. Additional serum in the matrix of the clot is thereby extracted and directed upwardly through the passageways of the filter. Downward motion of the filter finally stops when it is resting on a tightly packed cushion of cells and fibrin strands. Centrifugation is discontinued and the clear serum is poured or otherwise removed from the tube with the filter serving as a fixed barrier to prevent intermixing of the supernatant with the trapped cells, fibrin strands, and other particulates.

The filter is composed of a multiplicity of randomly-oriented generally-longitudinal fibers formed of a substantially biologically inert polymeric material having a specific gravity within the range of about 1.10 to 1.50 (preferably 1.20 to 1.40) and having fiber diameters within the range of about 10 to 40 (preferably 15 to 25) micrometers. The filter element should have a bulk density of approximately 0.20 to 0.60 grams per cubic centimeter and a diameter which permits it to be easily (rather than tightly) received within the mouth of a straight-sided cylindrical centrifuge tube. Such results may be achieved with a filter which, in an uncompressed state, has a diameter falling within the range of 85 to 110 percent of the tube's inside diameter. The length of the cylindrical filter should be 75 to 125 percent of its diameter.

The filter element may be supplied to the user as part of an assembly including a carrier cap. Such a cap is formed of flexible and stretchable plastic material and has a side wall defining an internal rib which engages and frictionally retains the filter element. The side wall has an outwardly flared skirt portion adapted to engage the mouth of a centrifuge tube and, upon such engagement, to help pilot the filter into the tube and, as insertion progresses, to expand outwardly causing the rib of the cap to release its hold on the filter. Insertion of the filter element is completed when the deformed cap encloses the upper portion of the tube and the internal rib assumes a latching position beneath the bead or lip of the centrifuge tube. The stretchable cap therefore serves as a filter retainer during transit, storage, and handling, a shield which performs a protective and guiding function as the filter element is inserted into the mouth of a centrifuge tube, and a cover which is capable of automatically releasing the filter element and then latching onto and sealing the mouth of the tube for subsequent processing of the blood sample.

Other objects, features, and advantages of the invention will become apparent from the specification and drawings.

DETAILED DESCRIPTION

Figure 1:
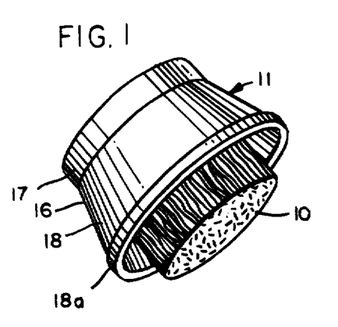
FIG. 1 is a perspective view of a filter and cap assembly embodying the invention.
Figure 2:
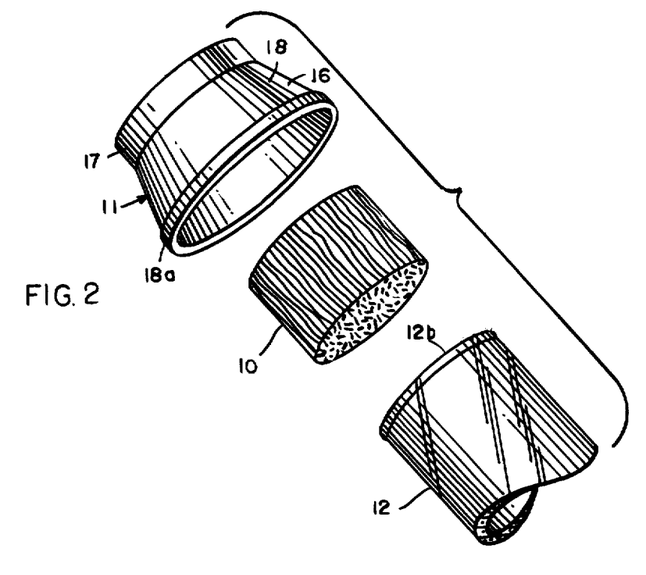
FIG. 2 is an exploded perspective view showing the filter, cap, and a portion of a conventional centrifuge tube.
Figure 3:
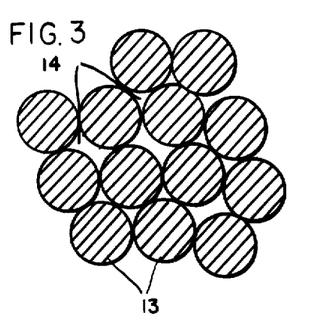
FIG. 3 is a greatly enlarged cross sectional view of a portion of the fibrous filter.

Referring to FIGS. 1–3, the numeral 10 generally designates a fibrous filter element for use in the centrifugally-activated separation of serum from other components of a blood sample. Cap 11 may be used as a carrier for the filter, to aid in inserting the filter into a blood-collection centrifuge tube 12, and to seal the open top of the tube when insertion of the filter element is completed.

Centrifuge tube 12 is a conventional open-topped glass tube of the type commonly used for the collecting and centrifuging of blood samples. Such a tube is presently commercially available in two sizes, specifically, 13×100 and 16×100, the approximate outside dimensions measured in millimeters. Ordinarily, such tubes are supplied to users in evacuated condition with piercable stoppers (not shown) sealing their open ends. Because the tube is air evacuated, the drawing of a blood sample from a patient (utilizing a syringe equipped with a double-ended needle, one end which is inserted into a vein and the other which is then driven through the piercable stopper) is facilitated. Such a procedure for collecting a blood sample, and the elements used for that purpose, are well known and widely used, and need not be described in further detail herein. It is to be noted, however, that while tube 12 would normally function as a blood collection tube as well as a centrifuge tube, only the latter function is considered particularly relevant with respect to the present invention since, quite conceivably, the blood sample might be collected by means of a standard plunger-equipped syringe and then transferred to tube 12.

In any event, tube 12 is cylindrical except for its rounded bottom end 12a (FIG. 10) and a slight but definite lip or enlargement 12b extending about the tube's mouth. The interior surfaces of the tube must be clean and free of lubricants and other coatings.

The filter element or plug 10 takes the form of a laterally compressible and expandable porous cylindrical body formed of a multiplicity of fibers 13 randomly oriented primarily in a longitudinal direction and defining a multiplicity of longitudinal flow passages 14 therebetween. The fibers 13 are composed of an inert polymeric material having a specific gravity within the range of about 1.10 to 1.50, the preferred range being 1.20 to 1.40. The term "insert" is used herein to mean a stable material that will not react with blood or with reagents and devices employed in the collection, storage, and analysis of blood, in any way that might alter the results of any of the variety of known tests for organic and inorganic constituents of serum. While cellulose acetate has been found particularly effective, other polymeric materials may also be used as, for example, ethyl cellulose, cellulose propionate, cellulose acetate butyrate, nylon (polyamides), polyvinyl chloride, and various copolymers of such materials, all formulated to have a specific gravity within the range of 1.10 to 1.50.

The fibers of the filter element have diameters within the range of about 10 to 40 micrometers ($\mu$m), the preferred range being 15 to 25 $\mu$m, and should be randomly oriented primarily in a longitudinal direction. The phrase "randomly oriented in a longitudinal direction" is used herein to have the same meaning as disclosed in the prior art (see, for example, U.S. Pat. No. 3,111,702);

that is, as a description of a condition of a body of fibers which are as a whole longitudinally aligned and generally parallel, but which nevertheless do have portions which are not in precise parallel alignment with adjacent fibers and which therefore contact such adjacent fibers at spaced-apart junctures or points of contact. Any given fiber in the cylindrical filter element 10 extends from one end face of the element to the opposite end face thereof; however, in doing so such fiber is not necessarily straight or parallel with adjacent fibers.

The fibers are held weakly or loosely together by a suitable binder which, like the fibers themselves, must be of a composition and extent so as not to interfere with the operation of the filter and with the test results. The binder simply functions to hold adjacent fibers together at their spaced-apart junctures or points of contact. The filter element must remain readily compressible and expandable, and the multiplicity of the fine passageways extending longitudinally through the element must not be occluded by the binder.

Where cellulose acetate is used as the fiber material, glycerol triacetate has been found to be particularly effective as the binder material. Glycerol triacetate is commonly used as a binder in the manufacture of other products, is considered ingestible and harmless, and has a specific gravity within the range of 1.15 to 1.16. If present in bound form (i.e., not as free or unattached particles within the fibrous structure) in an amount not exceeding 10% by weight of the filter element, and preferably at a level not exceeding 4%, it has been found that glycerol triacetate, when used as the binding agent for securing the fibers together at the nodes where adjacent fibers intersect, does not interfere with conventional tests for serum constituents such as calcium, inorganic phosphorus, glucose, blood urea nitrogen, uric acid, cholesterol, alkaline phosphatase, lactic dehydrogenase, albumin, and the like. Glycerol triacetate may also be used when materials other than cellulose acetate are used for the fibers and, conversely, other suitable binders may be used to bond the fibers (of any selected composition) together. Other binders include diethoxyethyl phthalate, dimethoxyethyl phthalate, triethyl citrate, tributyl citrate, tricresyl phosphate, glycerol tripropionate, triphenyl phosphate, ethyl glycolate, acetyl triiso hexyl citrate, acetyl triethyl citrate, dimethyl phthalate, diethyl phthalate, and triethyl phosphate.

Processes that may be used in the manufacture of filamentary tow from which filter elements of this invention may be made are already known in the art. Reference may be had to U.S. Pat. Nos. 3,095,343 and 3,111,702. The filter elements, whether manufactured by such procedure or by any other suitable technique, should have a diameter within the range of 9 to 15 millimeters, a length of from 75 to 125% of their diameter, and a bulk density within the range of 0.20 to 0.60 grams per cubic centimeter.

Within the range given, the particular diameter selected for the filter elements depends on the size of the tubes with which they are to be used. The filter elements should be small enough in diameter to be easily insertable into the tubes without first radially compressing such filters, yet must be large enough so that in use, during centrifugation, the filter elements will expand outwardly to produce an effective wiping action against the inside surfaces of the tubes. A tight fit at the time of insertion should be avoided because such frictional engagement, increased by the expansive forces exerted during centrifugation, may prevent downward movement of the filter elements towards the lower ends of the tubes during centrifugation. The desired relationship between a filter element and a tube at the time of insertion may be characterized as a loose or free sliding fit, it being understood that such a relationship may be achieved, despite substantial manufacturing tolerance ranges for both the tubes and the elements, because of the compressibility of such elements. For example, standard centrifuge tubes of 13×100 outside dimensions (in millimeters) have been found to have a considerable range of inside diameters averaging approximately 10.5 millimeters and, for use with such tubes, it has been found that filter elements averaging approximately 9.9 to 10.0 millimeters, with a variance either way of 0.4 millimeters, produce particularly effective results. In general, the diameter of the filter in an uncompressed state should fall within the range of 9 to 15 millimeters and should be 85 to 110 percent of the inside diameter of the centrifuge tube.

Filter length is important to insure adequate filtering and wiping actions and to prevent the filters from becoming tipped and canted within the tubes. Filters longer than approximately 125% of their diameter retain excessive volumes of serum, whereas filters shorter than approximately 75% of their diameter tend to be unstable within the centrifuge tubes, are likely to wipe inadequately or unevenly, and tend to allow fibrin strands and particulates to pass therethrough into the serum layer.

Figure 4:
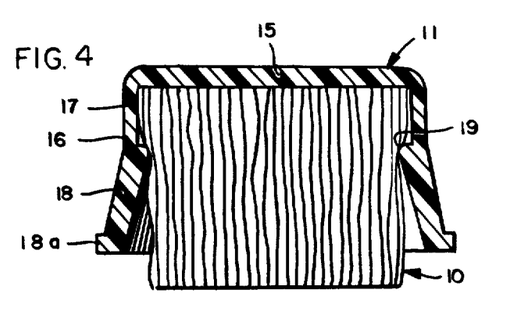
FIG. 4 is an enlarged longitudinal sectional view of the filter-cap assembly.

Cap 11 is fabricated from a soft, readily deformable and stretchable plastic such as low density polyethylene, silicone rubber, polyvinyl chloride, or other polymeric materials having their similar properties. The cap has an imperforate end wall 15 and a side wall 16, the latter including a generally cylindrical upper portion 17 and an outwardly and downwardly lower portion or skirt 18. As shown in FIG. 4, the upper cylindrical portion 17 is relatively thin. Not only is the skirt 18 of thicker cross section, but the dimensional difference appears as an annular internal rib or shoulder 19 at the juncture of the two portions. The internal diameter of the rib 19, that is, the diameter of the opening defined by that rib when the cap is in an untensioned or unstretched state, is smaller than the diameter of filter element 10 and the inside diameter of tube 12. The filter element is therefore frictionally retained in the cap as depicted in FIG. 4, with rib 19 causing slight inwardly deformation of the filter 10.

Figure 5:
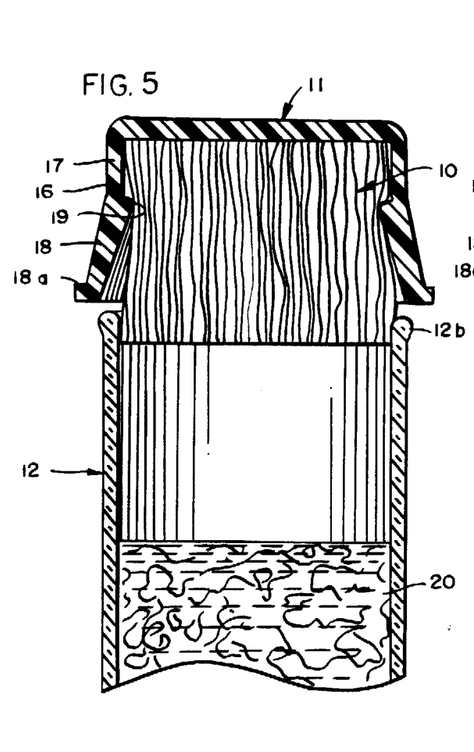
FIG. 5 is a sectional view similar to FIG. 4 but illustrating the relationship of the assembly with a centrifuge tube as the filter is being inserted into the tube.
Figure 6:
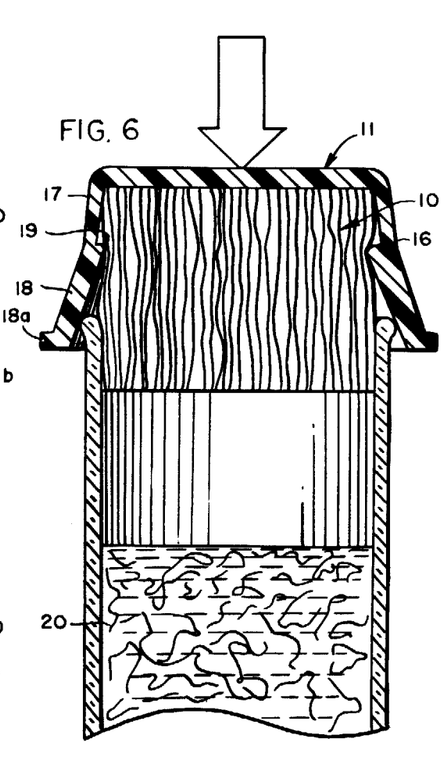
FIG. 6 is similar to FIG. 5 but shows the outward expansion of the skirt of the cap as filter insertion progresses.
Figure 7:
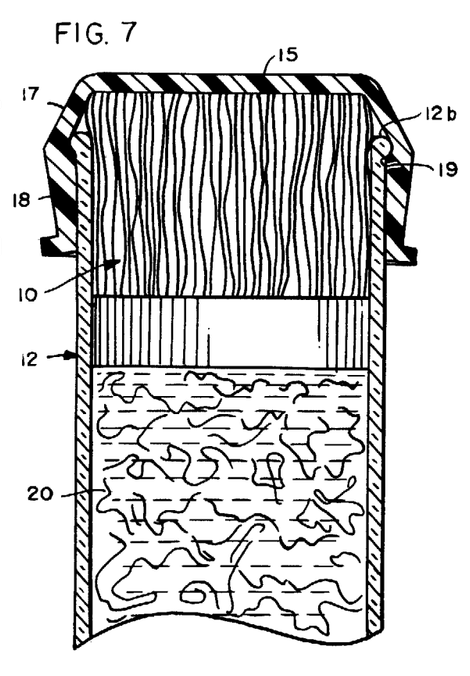
FIG. 7 is a longitudinal sectional view similar to FIGS. 4–6 but showing the filter in inserted position and the deformed cap in latched condition.

The flared skirt is dimensioned so that the inside diameter at its open end approximates the outside diameter of centrifuge tube 12. A user, gripping the cap-filter assembly by the cylindrical outer surface of the cap may easily direct the lower end of the filter into the mouth of the tube, bringing the lower surfaces of the skirt 18 into engagement with the lip of the tube (FIGS. 5 and 6). An annular flange 18a projecting outwardly from the lower end of the skirt may be provided to assist a user in orienting the cap in relation to the tube and to help protect against direct finger contact with the mouth of the tube, and with the sample of blood contained within the tube, as the cap-filter assembly is lowered. As force is exerted to continue the downward movement of the cap and filter, the rounded lip 12b of the tube bears against the sloping inside surface of the skirt 18 and causes outward expansion of the skirt (FIG. 6). At the same time, the filter element 10 proceeds further into the mouth of the tube and, because of the outward expansion or deformation of the side wall of the cap, rib 19 releases its hold on the filter element. As the cap is forced even further downwardly, the rib-providing portion of the cap expands outwardly to accommodate the upper end of tube 12 until rib 19 finally clears lip 12a and snaps into latching position beneath that lip (FIG. 7). It has been found that the tension of the cap, as the rib 19 snaps into its latching position, produces an audible sound to signal to the user that the filter element is fully inserted and a sealing of the tube's open end has been effected.

While cap 11 is valuable as a means for handling filter element 10, introducing that element into a centrifuge tube 12, and sealing that tube while simultaneously releasing the filter element within the tube, it is not essential that the cap be used as part of the operation of the filter element. If a user is willing to accept increased risks of exposure and contamination, and the further possibility that direct finger contact with a filter might have some effect on test results, he might simply insert such filter elements into the centrifuge tubes using his fingers to make direct contact with such elements. On the same basis, subsequent handling of the filter-equipped tube, and centrifuging of that tube and its contents, may be performed without any seal or cap at the tube's upper end. Regardless of whether cap 11 is or is not utilized, filter element 10 will be introduced into the open end of tube 12 only after a fresh sample of blood has already been received in that tube and only after coagulation of that blood has already occurred. Where tube 12 also functions as a blood collection tube, it has been found desirable to leave the original stopper in place following collection until after full coagulation has taken place. An interval of at least 30 minutes is generally required. Thereafter, the original stopper is removed, filter element 10 is inserted into the mouth of the tube, and the tube and its contents are centrifuged at rotational speeds commonly used in clinical laboratories for the centrifugation of blood. Quite typically, centrifugation would be performed at a relative centrifugal force (rcf) of 1100 or more for an interval of approximately 10 minutes.

As centrifugation commences, the cellular components of the blood are dispersed in the serum and are loosely entrapped in a three dimensional mesh of fibrin strands. This matrix or clot is then relatively free to descend, such descent being restrained primarily by weak bonds between the fibrin and the glass surfaces of the tube and by the elasticity of the fibrin which tends to resist deformation. As the clot matrix begins to descend, serum is displaced upwardly through the voids between the cells and fibrin. The clot concentrates at the lower end of the tube where, in the absence of the filter element as part of the system, such clot would retain a substantial volume of serum trapped in the voids between the cells and fibrin. During its descent the clot would, again in the absence of filter element 10, leave behind free fibrin strands, cellular materials, and other particulates in the serum, and other fibrin strands clinging to the inside surfaces of the tube.

Figure 8:
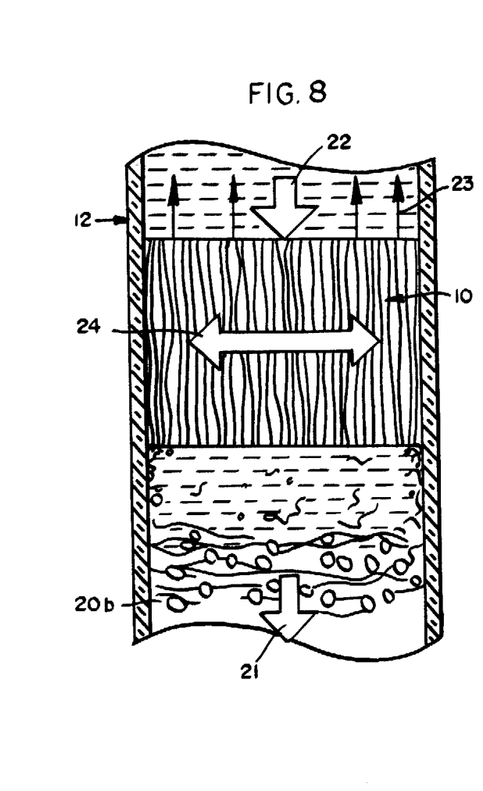
FIGS. 8 and 9 somewhat schematically depict the action of the filter during centrifugation.
Figure 9:
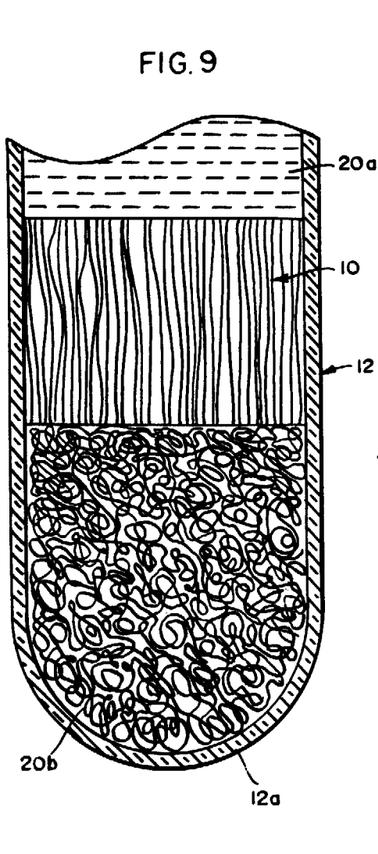

Descent and partial compaction of the clot takes place in advance of descent of the filter element 10. The filter element moves relatively slowly into the serum at the serum-air interface, the serum displacing air from the porous filter and causing outward expansion of the filter element into sliding frictional engagement with the inside surface of the tube. As serum displaces air from the filter element, the apparent density of the filter increases. The filter element descends, wiping the walls of the tube and pushing ahead loose cells and detached fibrin. The rate of descent of the filter element is believed to be limited largely by friction between the element and the walls of the tube and by fluid friction between the serum and the surfaces defining the minute passageways through the body of the element. The relationship between the descending clot and the trailing filter element during the early phase of centrifugation is somewhat schematically depicted in FIG. 8, where 20a represents the clarified serum, 20b designates the fibrin-cell matrix, arrows 21 and 22 indicate the direction of movement of the fibrin-cell matrix and the filter element, respectively, arrows 23 represent the direction of flow of serum through the filter element, and arrow 24 indicates the lateral expansion of the filter element, and the forceful wiping contact between that element and the inside surface of tube 12, occasioned by resistance to the flow of serum through the element's minute longitudinal passages.

Figure 10:
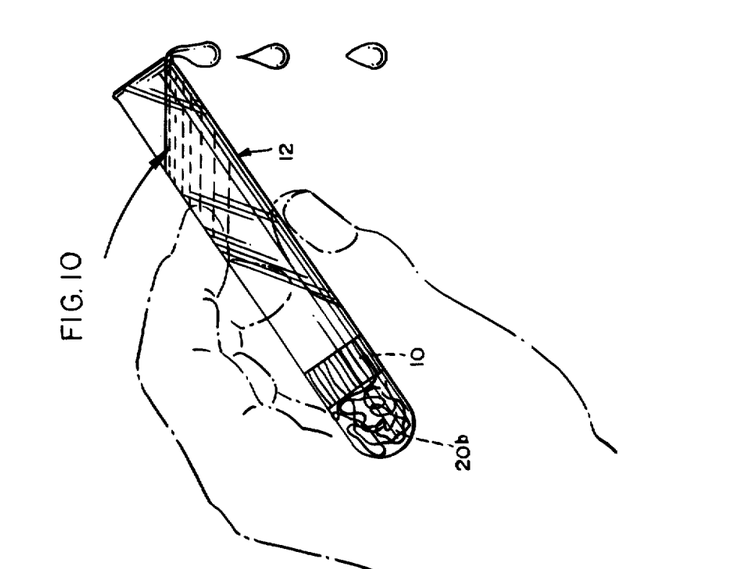
FIG. 10 illustrates the function of the filter as a particulate-retaining barrier during pour-off of the serum from the tube.

Ultimately, the filter element contacts the clot or fibrin-cell matrix 20b, such contact occurring well after the filter element enters the lower half of the tube. Since the specific gravity of the material from which the filter is formed is substantially greater than that of the blood's cellular components, the filter element begins to compress the fibrin-cell matrix 20b to squeeze additional amounts of serum therefrom. The fact is supported by the observation that the yield of serum as a result of centrifugation is greater when a filter element is used, in comparison with a straight-spin down without use of a filter element, even where the filter element is formed of a hydrophilic material (such as cellulose acetate) and therefore tends to retain a volume of serum in its interstices. Downward motion of the filter element 10 eventually stops with the element resting on a tightly packed cushion of fibrin and cells (FIG. 10). Following removal of cap 11 from the tube, the supernatant serum 20a may be poured or pipetted from the tube, the filter element 10 remaining in place as a barrier to prevent re-mixing of the serum and cellular components.

While the filter element does perform a filtering function as well as a wiping action, calculations reveal that the pores of passageways extending generally longitudinally through the element are large enough to permit red cells, which are highly deformable, to pass therethrough under certain conditions without rupture of the cell membranes. The fact that such cells do not do so under normal operating conditions is believed to be attributed in a large part to the lag in the descent of the filter element 10 with respect to clot 20b, the relatively slow descent of the filter element occasioned by the frictional forces generated between element 10 and the inside surface of the tube, the lateral expandability of the element resulting from the longitudinal orientation of the fibers and the limited bonding therebetween, and the length of the filter element in relation to its diameter. It is to be noted that if a blood sample fails to clot prior to centrifugation as, for example, where the sample has been drawn from a hemophiliac or from a patient on anticoagulant therapy, red cells do pass into and through filter element 10 and their presence in the fluid above the filter element following centrifugation, and the bottoming of the filter element in the tube (with no visible red cells therebelow), clearly signal the special circumstance presented.

The following example of a preferred embodiment and mode of practicing the invention is given for purposes of illustration.

EXAMPLE

The performance of filter elements embodying this invention, and the effectiveness of the method of using such filter elements, were evaluated for 32 standard blood chemistry tests. The analytical equipment used for conducting such tests included a SMA 12/60 analyzer (Technicon Instruments Corporation, Tarrytown, N.Y.) for calcium, inorganic phosphorus, glucose, blood urea nitrogen, uric acid, cholesterol, total protein, albumin, total bilirubin, alkaline phosphatase, lactic dehydrogenase, and serum glutamate-oxaloacetate transaminase, a duPont ACA (duPont, Wilmington, Del.), for assaying values for carbon dioxide, creatinine, creatine phosphokinase, chloride, lipase, amalase, pseudocholinesterase, magnesium, iron, acid phosphatase, triglyceride, glutamate-oxaloacetate transaminase and lactic acid, and an Auto Analyzer II (Technicon Instruments Corporation, Tarrytown, N.Y.) for sodium, potassium, and phosphorus. Four tubes of blood were collected from each of eight donors using 16×100 millimeter evacuated collection tubes in accordance with the manufacturer's instructions (Becton-Dickinson, Rutherford, N.J.). One specimen from each donor was processed using a filter element embodying the invention, as described below, a second specimen was processed using a commercial gel separator (Sure-Sep II Separator, General Diagnostics, Morris Plains, N.J.), a third by using a commercial rubber disk separator (Glasrock Filter Sampler, Glasrock Products, Inc., Fairburn, Ga.), and the fourth by using no separator at all.

The filter elements embodying the invention were composed of generally longitudinally-oriented cellulose acetate fibers bonded together at spaced-apart junctures by a glycerol triacetate binder. Prior to use the filter elements were heated to a temperature of approximately 140° C. to volatilize and remove free unbonded glycerol triacetate therefrom. The residual bound glycerol triacetate securing the fibers together at their crossing nodes was determined to be less than 8% by weight.

Each filter was cylindrical in configuration with a diameter of approximately 13.6 millimeters, a length of approximately 11.0 millimeters, and a bulk density of 0.232 grams per cubic centimeter. The fibers were estimated to have an average diameter of approximately 0.25 micrometers and a specific gravity of 1.32. The average inside diameters of the blood-collecting centrifuge tubes was determined to be about 13.6 millimeters.

The compressible fibrous filter elements were releasably supported by stretchable filter caps similar to the caps depicted in FIGS. 1 and 4, such caps being formed from low density polyethylene (NA270, USI, New York, N.Y.). The inside diameter of such caps, measured at the internal ribs thereof when such caps were unstretched, was approximately 13.2 millimeters.

The procedure for those specimens to be processed using the cellulose acetate filters consisted of allowing each tube with a freshly-drawn specimen to stand approximately 30 minutes for clotting, then removing the rubber stopper from the blood collection tube and inserting a filter into the open end of the tube utilizing the filter cap as the element-inserting device, then forcing the cap downwardly over the end of the tube to secure the stretched cap in place with the lower end of the filter element spaced just above the surface of the sample, then centrifuging the tube and its contents at 1100 rcf for 10 minutes, then inspecting the tube and its contents for hemolysis, barrier condition and serum appearance, and finally pipetting amounts of serum from the tube for the various blood chemistry tests. The procedures for those specimens to be processed with commercial gel separators and rubber disk separators were in accordance with the manufacturer's instructions. All samples were compared for serum yield.

From visual inspections of the tubes containing the cellulose acetate filters, following centrifugation of those tubes, it was found that the fibrous filters caused no apparent hemolysis. In each instance, the fibrous filter was found to be resting upon a compacted fibrin-cell maxtrix at the lower end of the tube, having wiped the inside surfaces of the tube during its descent to remove fribrin and other particulate matter therefrom. The serum layer in each tube in which a fibrous filter was used was clear and substantially fibrin-free. In some cases, fibrin would penetrate through the filter into the serum; however, the serum could still be decanted because the fibrin would remain firmly attached to the filter. Serum yield measurements showed that those specimens processed with the fibrous filters provided a yield that was essentially the same as those specimens processed with gel separators, and an average of 15% greater than those samples processed with rubber disk filters. In all instances in which the fibrous filters were used, serum could be easily poured from the tubes without dislodging the filter barriers from those tubes.

The data from the blood chemistry tests was analyzed statistically using the paired t-test method where the bias, standard deviation, t-value, and P-value were calculated. Most of the tests showed no statistically significant differences (biases). In those tests which showed statistically significant differences, such differences were judged to be small and not clinically significant. In such latter group were alkaline phosphatase, carbon dioxide, cholesterol, SPK, glucose, LDH, sodium, total protein, uric acid, and potassium. In total, no clinically significant differences were observed between the specimens processed with the fibrous cellulose acetate filters and those processed with no separators at all. Use of the fibrous filters did appear to give significantly better results in many analytical values than the use of gel or rubber disk separators.

While in the foregoing I have disclosed an embodiment of the invention in considerable detail for purposes of illustration, it will be understood by those skilled in the art that many of these details may be varied without departing from the spirit and scope of the invention.

I claim:

1. A filter element for insertion into a centrifuge tube containing clotted whole blood for separating serum from the cellular and fibrous components, comprising a laterally compressible and expandable cylindrical body formed of a multiplicity of fibers randomly oriented primarily in a longitudinal direction and defining generally longitudinal flow passages therebetween; said fibers being composed of an inert polymeric material of a specific gravity between 1.10 to 1.50 and being bonded together at spaced-apart junctures by a bonding agent; said fibers having diameters within the range of about 10 to 40 micrometers and said body having a bulk density of 0.20 to 0.60 grams per cubic centimeter, a diameter of 9 to 15 millimeters, and a length of from 75 to 125% of said diameter; said polymeric material being cellulose acetate and said binding agent being glycerol triacetate; said glycerol triacetate being present in said filter element at a percentage by weight no greater than 10%.

2. The filter element of claim 1 in which said glycerol triacetate is present in said filter element at a percentage by weight no greater than 4%.

3. The filter element of claim 1 in which said fibers have diameters within the range of 15 to 25 micrometers.

4. The combination comprising an open-topped glass centrifuge tube and a fibrous cylindrical filter element receivable in said tube; said filter element being laterally compressible and expandable and being formed entirely of a multiplicity of fibers randomly oriented primarily in a longitudinal direction and bonded together only at spaced-apart junctures to define a multiplicity of generally longitudinal flow passages through said element; said fibers being composed of an inert polymeric material of a specific gravity between 1.10 to 1.50, and having diameters within the range of about 10 to 40 micrometers; said element having a bulk density of 0.20 to 0.60 grams per cubic centimeter and a length of from 75 to 125% of the diameter thereof; said centrifuge tube having a substantially uniform inside diameter throughout its length; said diameter of said filter element in an unexpanded and uncompressed state falling within 85 to 110% of said inside diameter of said tube; said fibers of said filter element being bonded together at spaced-apart junctures by a binding agent; said polymeric material being cellulose acetate and said binding agent being glycerol triacetate; said glycerol triacetate being present to an extent no greater than 10% by weight of said filter element.

5. The combination of a serum filter element and a supporting cap therefor, said filter element comprising a laterally compressible and expandable cylindrical body consisting essentially of a multiplicity of fibers randomly oriented primarily in a longitudinal direction and bonded together only at spaced-apart junctures to define generally longitudinal flow passages therebetween; said fibers being composed of an inert polymeric material of a specific gravity between 1.10 and 1.50, and having diameters within the range of about 10 to 40 micrometers; said cap being formed of resilient stretchable plastic material having a top wall and an integral depending side wall extending about said filter element; said side wall being provided with an inwardly-projecting rib frictionally engaging said filter element to retain the same within said cap when said side wall is unstretched; said side wall being stretchable outwardly to an extent sufficient to release said filter element; said side wall including a downwardly and outwardly flared skirt portion terminating in an enlarged opening at the bottom of said cap, said opening being dimensioned to receive the upper end of a centrifuge tube for enlarging said side wall and releasing said filter element into such tube when said cap is forced downwardly over the tube's upper end.

6. The combination of claim 5 in which said rib is annular and defines an opening having a diameter smaller than the diameter of said filter element in an uncompressed state.

7. The combination of claim 5 in which said filter element has a bulk density within the range of about 0.20 to 0.60 grams per cubic centimeter.

8. The combination of claim 5 in which said filter element when undistorted has a diameter within the range of 9 to 15 millimeters and a length of from said 75 to 125% of said diameter.

9. The combination of claim 5 in which said fibers of said filter element are formed of a polymeric material having a specific gravity within the range of 1.20 to 1.40.

10. The combination of a serum filter element and a supporting cap therefor, said filter element comprising a laterally compressible and expandable cylindrical body consisting essentially of a multiplicity of fibers randomly oriented primarily in a longitudinal direction and bonded together only at spaced-apart junctures to define generally longitudinal flow passages therebetween; said fibers being composed of an inert polymeric material of a specific gravity between 1.10 and 1.50, and having diameters within the range of about 10 to 40 micrometers; said cap being formed of resilient stretchable plastic material having a top wall and an integral depending side wall extending about said filter element; said side wall being provided with an inwardly projecting rib frictionally engaging said filter element to retain the same within said cap when said side wall is unstretched; said side wall being stretchable outwardly to an extent sufficient to release said filter element; said side wall also including a downwardly and outwardly flared skirt portion terminating in an enlarged opening at the bottom of said cap; said opening being dimensioned to receive the upper end of a centrifuge tube for enlarging said side wall and releasing said filter element into such tube when said cap is forced downwardly over the tube's upper end; and a centrifuge tube having an inside diameter larger than the diameter of said filter element and an outside diameter capable of being received within said enlarged opening of said cap.

11. The combination of claim 10 wherein said centrifuge tube includes an external lip at the upper end thereof; said side wall of said cap being stretchable outwardly to an extent sufficient to position said rib beneath said lip to latch said cap upon said tube.

12. A method of treating a sample of blood to separate clear serum therefrom, comprising the steps of collecting a sample of blood and allowing the same to coagulate in a centrifuge tube to form a fibrin-cell clot therein; then inserting a laterally-expandable, porous and fibrous cylindrical filter element into said tube and centrifuging said tube and its contents to cause said element to descend towards the bottom of said tube behind said clot while allowing serum to flow longitudinally upwardly through the pores of said element; said element being composed of a multiplicity of fibers randomly oriented primarily in a longitudinal direction and formed of an inert polymeric material having a specific gravity within the range of 1.10 to 1.50; said fibers having diameters within the range of about 10 to 40 micrometers and said filter element having a bulk density of about 0.20 to 0.60 grams per cubic centimeter; and continuing centrifugation of said tube and its contents until said filter element engages and compresses said clot within the lower portion of said tube.

13. The method of claim 12 in which the specific gravity of said polymeric material of said fibers falls within the range of 1.20 to 1.40.

14. The method of claim 12 in which said polymeric material is selected from the group consisting of cellulose acetate, ethyl cellulose, cellulose propionate, cellulose acetate butyrate, nylon, and polyvinyl chloride.

15. The method of claim 14 in which adjacent fibers of said filter element are bonded together at spaced-apart junctures.

16. The method of claim 15 in which said adjacent fibers are bonded together at spaced-apart junctures by a binding agent selected from the group consisting of glycerol triacetate, diethoxyethyl phthalate, dimethoxyethyl phthalate, triethyl citrate, tributyl citrate, tricresyl phosphate, glycerol tripropionate, triphenyl phosphate, ethyl glycolate, acetyl triiso hexyl citrate, acetyl triethyl citrate, dimethyl phthalate, diethyl phthalate, and triethyl phosphate.

17. The method of claim 16 in which said polymeric material is cellulose acetate and said binding agent is glycerol triacetate.

18. The method of claim 12 in which said filter element expands outwardly into wiping engagement with the inner surface of said tube in response to the invasion of serum between the fibers thereof upon commencement of centrifuging step.

19. A method of treating a coagulated sample of blood in an open-topped centrifuge tube to separate clear serum from the clot of fibrin and cellular components, comprising the steps of inserting a laterally-expandable, porous, cylindrical filter element into the open top of said tube and then centrifuging said tube and its contents to cause said element to descend towards the bottom of said tube behind said clot while allowing serum to flow upwardly into and through said element; said element being formed of a multiplicity of fibers randomly oriented primarily in a longitudinal direction and bonded together only at spaced-apart junctures; said fibers being composed of an inert polymeric material having a specific gravity greater than any of the constituents of said blood sample; said polymeric material of said fibers being cellulose acetate and said fibers being bonded together at said spaced-apart junctures by glycerol triacetate; and continuing said centrifugation until said filter element engages and compresses said clot within the lower portion of said tube.

20. A method of treating a sample of coagulated blood contained in an open-topped centrifuge tube for the purpose of separating clear serum from the fibrin-cellular clot therein, comprising the steps of positioning a cap having a depending stretchable annular side wall above the open top of said tube, said stretchable side wall including a cylindrical upper portion, a downwardly flared skirt portion, and an internal rib therebetween, said rib defining an opening smaller than the inside of said tube when said side wall is in an unstretched state, said rib engaging and releasably holding a cylindrical filter element dimensioned to be axially received within said tube through the open top thereof, then lowering said cap over the open end of said tube to insert said filter element into said tube and bring the inside surface of said skirt portion and said rib into engagement with the outside of said tube at the top thereof, then forcing said cap downwardly over said tube to cause said side wall to stretch outwardly and release said filter element within said tube.

21. The method of claim 20 in which said tube has a lip extending about the open top thereof, and in which there is the further step of continuing to force said cap downwardly over said tube until said rib is located beneath said lip, thereby latching said cap upon the upper end of said tube.

22. The method of claim 20 or 21 in which there is the further step of centrifuging said tube and its contents to cause said filter element to travel towards the bottom of said tube behind said clot, while allowing serum to flow upwardly into and through said filter element.

23. The method of claim 22 in which said filter element is formed of a multiplicity of fibers randomly oriented primarily in a longitudinal direction and bonded together at spaced-apart junctures to define a multiplicity of longitudinal flow passages between said fibers, said fibers being composed of an inert polymeric material having a specific gravity greater than the constituents of blood.

24. A method of treating a sample of coagulated blood contained in an open-topped centrifuge tube for the purpose of separating clear serum from the fibrin-cellular clot therein, comprising the steps of positioning a cap having a depending stretchable annular side wall above the open top of said tube, said stretchable side wall including a cylindrical upper portion, a downwardly flared skirt portion, and an internal rib therebetween, said rib defining an opening smaller than the inside of said tube when said side wall is in an unstretched state, said rib engaging and releasably holding a cylindrical filter element dimensioned to be axially received within said tube through the open top thereof, said filter element being formed of a multiplicity of fibers randomly oriented primarily in a longitudinal direction and bonded together at spaced-apart junctures to define a multiplicity of longitudinal flow passages between said fibers, said fibers being composed of an inert polymeric material having a specific gravity within the range of 1.10 to 1.50, said fibers having a diameter within the range of 10 to 40 micrometers, and said filter element having a bulk density within the range of 0.20 to 0.60 grams per cubic centimeter, then lowering said cap over the open end of said tube to insert said filter element into said tube and bring the inside surface of said skirt portion into engagement with the top of said tube, then forcing said cap downwardly over said tube to cause said side wall to stretch outwardly and release said filter element within said tube, and centrifuging said tube and its contents to cause said filter element to travel towards the bottom of said tube behind said clot, while allowing serum to flow upwardly into and through said filter element.

25. The method of claim 24 in which said filter element has a length of from 75 to 125% of the diameter thereof.

* * * * *